United States Patent [19]

Shine

[11] 4,264,731

[45] Apr. 28, 1981

[54] DNA JOINING METHOD

[75] Inventor: John Shine, San Francisco, Calif.

[73] Assignee: The Regents of the University of California, Berkeley, Calif.

[21] Appl. No.: 898,887

[22] Filed: Apr. 21, 1978

Related U.S. Application Data

[63] Continuation-in-part of Ser. No. 805,023, Jun. 9, 1977, which is a continuation of Ser. No. 801,343, May 27, 1977.

[51] Int. Cl.² .................. C12P 19/34; C12N 15/00; C12R 1/19
[52] U.S. Cl. .................................. 435/91; 435/172; 435/317; 435/849
[58] Field of Search ................. 195/1, 28 N; 435/91, 435/172, 317

[56] References Cited

PUBLICATIONS

Molecular Cloning of Recombinant DNA, Miami Winter Symposium, vol. 13, pp. 35-56 (1977).

*Primary Examiner*—Alvin E. Tanenholtz
*Attorney, Agent, or Firm*—Keil & Witherspoon

[57] ABSTRACT

A selected portion of DNA molecules having reactant ends which are capable of being joined in a ligase catalyzed reaction are pretreated so as to remove the 5'-terminal phosphate groups. Such a treatment reduces the frequency of joining an undersired combination and enhances the frequency of joining the desired combination.

10 Claims, 1 Drawing Figure

DNA JOINING METHOD

The Government has rights in this invention pursuant to Grants No. GM-21830 and CA-14026 awarded by the Department of Health, Education and Welfare.

This application is a continuation-in-part of copending application Ser. No. 805,023, filed June 9, 1977 which is a continuation of copending application Ser. No. 801,343, filed May 27, 1977.

BACKGROUND AND PRIOR ART

The constellation of techniques known as recombinant DNA technology includes among its basic elements processes for cutting DNA strands and also for joining DNA strands. By appropriate means, specific fragments of DNA from one organism can be covalently joined with specific fragments derived from a wholly unrelated organism. Such composite, or recombinant, DNA can, under appropriate conditions be transferred to and replicated in a microorganism, thereby conferring upon that organism genetic properties which it would be extremely unlikely to acquire by normal biological mating processes. The potential for practical application of recombinant DNA technology is enormous and far reaching.

DNA is a linear polymer composed of nucleotide subunits. DNA in its native form is made up of two polynucleotide strands of complementary base sequence wound around each other in a right handed double helix, as is well known in the art. DNA may exist in the form of straight chains having two ends or in the form of endless loops. Loops may be converted to straight chains and straight chains may be converted to shorter fragments by the introduction of double-strand chain breaks, which may be produced for example by hydrolysis of the phosphodiester bonds linking adjacent nucleotides. Specific break points, susceptible to one or more enzymes of the type known as restriction endonucleases, may occur in a given nucleotide sequence. Where the strand breaks occur opposite each other on the component strands of the double helix, the break results in blunt-ended strands. However, if the individual strand breaks are staggered by a distance of a few nucleotides, the resulting molecules will have single-stranded, self-complementary ends, sometimes termed cohesive ends.

DNA molecules may be joined end to end by reactions catalyzed by enzymes generically termed ligases. Certain ligases are specific for the joining of DNA molecules having cohesive ends. Others are also capable of joining blunt-ended molecules. In a reaction mixture in which it is desired to join DNA molecules having specific sequences derived from different sources, a reaction mixture is formed containing molecules of the first sequence together with DNA molecules of the second sequence and the appropriate ligase. The DNA ends potentially capable of being joined, termed reactant ends herein, can join in a variety of combinations. In these circumstances, competing joining reactions other than the desired joining can and do occur. Molecules of the first sequence may join with each other, or individual linear molecules may join head-to-tail to form monomer rings, and other higher order joining reactions may compete with the desired reactions. As a result, formation of the desired recombinant molecule may be a relatively improbable event so that only a small fraction of the product molecules are of the desired type.

Prior art attempts to deal with this problem have been indirect and incomplete. In some cases it has been possible to bias the reaction conditions in such a way that the desired product is more favored, or to rely upon physical separation techniques to separate some of the undesired reaction products. In addition, the sophisticated selection techniques of microbial genetics have made it possible to detect certain low frequency recombinants. Where applicable, the latter technique has been extremely valuable. However, such methods are not applicable in all situations and they are tedious to apply.

In recombinant DNA technology, small autonomously replicating DNA molecules in the form of closed loops, termed plasmids, are exploited. The DNA to be recombined with the plasmid may be obtained in a variety of ways, although Federal safety requirements have made the in vitro formation of DNA complementary to isolated mRNA the method of choice. Such DNA is termed cDNA.

Recombinant plasmids are formed by mixing restriction endonuclease-treated plasmid DNA with cDNA containing end groups similarly treated. In order to minimize the chance that segments of cDNA will form combinations with each other, the plasmid DNA is added in molar excess over the cDNA. In prior art procedures this has resulted in the majority of plasmids circularizing without an inserted cDNA fragment. The subsequently transformed cells contained mainly plasmid and not cDNA recombinant plasmids. As a result, the selection process was very tedious and time consuming. The prior art solution to this problem has been to attempt to devise DNA vectors having a restriction endonuclease site in the middle of a suitable marker gene such that the insertion of a recombinant divides the gene thereby causing loss of the function coded by the gene.

SUMMARY OF THE INVENTION

The present invention is a method for treating DNA molecules that are to be combined in a subsequent joining reaction, such that the frequency of joining an undesired combination is reduced and the frequency of joining the desired combination is enhanced. Specifically, the method involves the pretreatment of the reactant ends of the DNA to be joined to effect removal of certain 5' terminal phosphate groups. The ligase catalyzed reaction is dependent upon the existance of a 5' phosphate at the end to be joined. Joining is therefore prevented between pairs of reactant end groups from which the 5' terminal phosphate has been removed.

The general method has been applied in two different circumstances. In the first circumstance, circular plasmid DNA is rendered linear by a double-strand scission and mixed with linear DNA in order to form a recombinant between the linear DNA and the plasmid. A major competing reaction, the head-to-tail joinder of the plasmid to reconstitute the closed loop without recombination with another DNA molecule, is prevented. In a second circumstance, linear DNA is subjected to chain scission to produce two sub-fragments which are to be purified separately, then rejoined. A major competing reaction, the rejoinder of the sub-fragments in opposite sequence from their original sequence, is prevented by application of the method of the present invention.

DETAILED DESCRIPTION OF THE INVENTION

Figure 1:
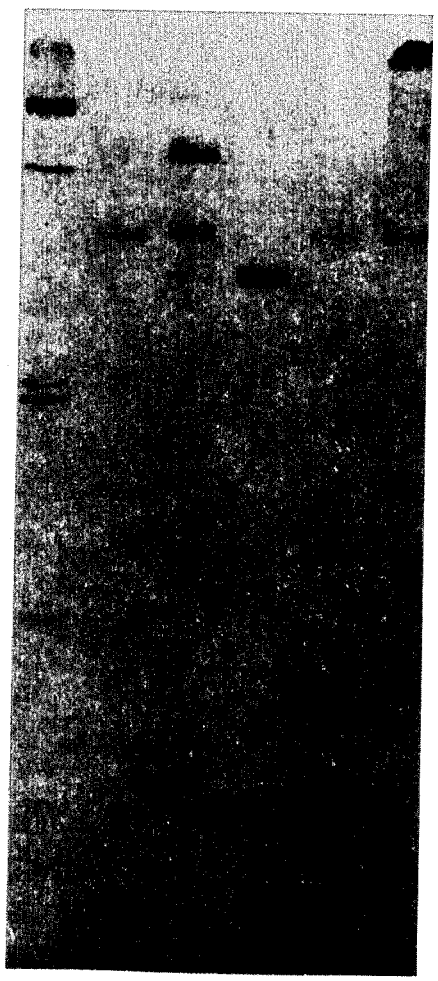

The present invention is based on the fact that the DNA ligase catalyzed reaction takes place between a 5'-phosphate DNA end group and a 3'-hydroxyl DNA end group. If the terminal 5'-phosphate is removed, no joining reaction occurs. Where double-stranded DNA is to be joined, three situations are possible, as shown in Table 1.

TABLE 1

| Case | Reactants | | Ligase Product | |
|---|---|---|---|---|
| I | ———OH 3'  H$_2$O$_3$PO——— 5' | | ———O—P—O——— 3'  5' | + 2H$_2$O |
|   | + | | | |
|   | ———OPO$_3$H$_2$ 5'  HO——— 3' | | ———O—P—O——— 5'  3' | |
| II | ———OH 3'  H$_2$O$_3$P—O——— 5' | | ———O—P—O——— 3'  5' | + H$_2$O |
|   | + | | | |
|   | ———OH 5'  OH——— 3' | | ———OH 5'  HO——— 3' | |
| III | ———OH 3'  HO——— 5' | | no reaction | |
|   | + | | | |
|   | ———OH 5'  HO——— 3' | | | |

In Table 1, double-stranded DNA is schematically represented by solid parallel lines, while their respective 5' and 3' end groups are labeled with hydroxyl (OH) or phosphate (OPO$_3$H$_2$), as the case may be. In case I, 5' phosphates occur on both reactant ends with result that both strands become covalently joined. In case II only one of the strands to be joined has a terminal 5' phosphate, with the result that a covalent single-strand linkage occurs leaving a single-strand break or discontinuity on the other strand. The strand not covalently joined remains associated with the joined molecule by virtue of the hydrogen bonding interactions between complementary base-pairs on opposite strands, as is well known in the art. In case III neither of the reactant ends has a 5'-phosphate and no joining reaction can occur.

Unwanted joining reactions can be prevented therefore by treatment of the appropriate reactant ends, whose joining is to be prevented, to remove the 5'-phosphate groups therefrom. Any method suitable for removal of 5'-phosphate groups that does not otherwise damage the DNA structure may be employed. Hydrolysis catalyzed by the enzyme alkaline phosphatase is preferred.

As part of the present invention, a novel method for reducing the number of colonies to be screened for recombinant plasmids has been devised. The method involves treating restriction endonuclease cleaved plasmid DNA with alkaline phosphatase, an enzyme commercially available from several sources, such as Worthington Biochemical Corporation, Freehold, New Jersey. Alkaline phosphatase treatment removes the 5'-terminal phosphates from the endonuclease generated ends of the plasmid and prevents self-ligation of the plasmid DNA. Consequently, circle formation, hence transformation, will be dependent on the insertion of a DNA fragment containing 5'-phosphorylated termini. The described process reduces the relative frequency of transformation in the absence of recombination to less than 1 in 10$^4$.

A second embodiment of the invention has been developed for use in the situation where a linear DNA molecule is to be cleaved into two sub-fragments, typically with the use of a restriction endonuclease enzyme, then reconstituted in the original sequence. Preparations of cDNA of uniform length can be made as described in copending application Ser. No. 836,218, incorporated herein by reference. The desired nucleotide sequence may be further purified from contaminating sequences of the same overall length by treatment with a restriction endonuclease capable of acting internally upon the desired sequence, which will result in cleavage of the desired sequence into two sub-fragments, most probably of unequal length. These sub-fragments upon electrophoresis will from two discrete bands at positions corresponding to their respective lengths, the sum of which will equal the length of the polynucleotide prior to cleavage. Contaminants in the original band that are not susceptible to the restriction enzyme may be expected to migrate to the original position. Contaminants containing one or more recognition sites for the enzyme may be expected to yield two or more sub-fragments. Since the distribution of recognition sites is believed to be essentially random, the probability that a contaminant will also yield sub-fragments of the same size as those of the fragment of desired sequence is extremely low. The amount of material present in any band of radioactively labeled polynucleotide can be determined by quantitative measurement of the amount of radioactivity present in each band, or by any other appropriate method. A quantitative measure of the purity of the fragments of desired sequence can be obtained by comparing the relative amounts of material present in those bands representing sub-fragments of the desired sequence with the total amount of material.

Following the foregoing separation, the desired sequence may be reconstituted. The enzyme DNA ligase, which catalyzes the end-to-end joining of DNA fragments, may be employed for this purpose. The gel electrophoresis bands representing the sub-fragments of the desired sequence may be separately eluted and combined in the presence of DNA ligase, under the appropriate conditions. See Sgaramella, V., Van de Sande, J. H., and Khorana, H. G., *Proc. Natl. Acad. Sci USA* 67, 1468 (1970). Where the sequences to be joined are not blunt-ended, the ligase obtained from *E. Coli* may be used, Modrich, P., and Lehman, I. R., *J. Biol. Chem.* 245, 3626 (1970).

The efficiency of reconstituting the original sequence from sub-fragments produced by restriction endonuclease treatment will be greatly enhanced by the use of a method for preventing reconstitution in improper sequence. This unwanted result is prevented by treatment of the homogeneous length cDNA fragment of desired sequence with an agent capable of removing the 5'-terminal phosphate groups on the cDNA prior to cleavage of the homogeneous cDNA with a restriction endonuclease. The enzyme, alkaline phosphatase, is preferred. The 5'-terminal phosphate groups are a structural prerequisite for the subsequent joining action of DNA ligase used to reconstitute the cleaved sub-fragments. Therefore, ends which lack a 5'-terminal phosphate cannot be covalently joined. The DNA sub-fragments can only be joined at the ends containing a 5'-phosphate generated by the restriction endonuclease cleavage performed on the isolated DNA fragments.

The foregoing process prevents the formation of the most significant unwanted joining reaction, namely the joining of the two fragments in reverse sequence, back-to-front instead of front-to-back. Other possible side reactions, such as dimer formation and cyclization are not prevented, since these can occur by a reaction of type II, supra, Table 1. Such side reactions are less troublesome, however since they lead to physically separable and identifiable products, whereas recombination in reverse order does not.

Having described in principle the operation of the method, specific details are next presented by way of example.

EXAMPLE 1

The formation of a recombinant plasmid and its characterization after replication is described. Plasmid pMB-9 DNA, prepared as described by Rodriguez, R. L., Boliver, F., Goodman, H. M., Boyer, H. W., and Betlach, M., in ICN-UCLA Symposium on Molecular and Cellular Biology, D. P. Wierlich, W. J. Rutter, and C. F. Fox, Eds., (Academic Press, New York 1976) pp. 471-477, was cleaved at the Hind III restriction site with Hsu I endonuclease, then treated with alkaline phosphatase, type BAPF, Worthington Biochemical Corporation, Freehold, New Jersey. The enzyme was present in the reaction mixture at the level of 0.1 unit/microgram DNA and the reaction mixture was incubated in 25 mM Tri-HCl, for pH 8 for 30 minutes at 65° C., followed by phenol extraction to remove the phosphatase. After ethanol precipitation, the phosphatase treated plasmid DNA was added to cDNA containing Hind III cohesive termini at a molar ratio of 3 moles plasmid to 1 mole cDNA. The mixture was incubated in 66 mM Tris, pH 7.6, 6.6 mM $MgCl_2$, 10 mM dithiothreitol, and 1 mM ATP for one hour at 14° C. in the presence of 50 units/ml of T4 DNA ligase.

The ligation mixture was added directly to a suspension of E. Coli X-1776 cells prepared for transformation as follows: Cells were grown to a cell density of about $2 \times 10^8$ cells/ml in 50 ml of medium containing Tryptone 10 g/l, yeast extract 5 g/l, NaCl 10 g/l, NaOH 2 mM, diaminopimelic acid 100 μg/ml and thymine 40 μg/ml, at 37° C. Cells were harvested by centrifugation for 5 minutes at $5,000 \times G$ at 5° C., resuspended in 20 ml cold NaCl 10 mM, centrifuged as before and resuspended in 20 ml transformation buffer containing 75 mM $CaCl_2$, 140 mM NaCl and 10 mM Tris pH 7.5, and allowed to remain 5 minutes in ice. The cells were then centrifuged and resuspended in 0.5 ml transformation buffer. Transformation was carried out by mixing 100 μl of the cell suspension with 50 μl recombinant DNA (1 μg/ml). The mixture was incubated at 0° C. for 15 minutes, then transferred to 25° C. for 4 minutes, then at 0° C. for 30 minutes. The cells were then transferred to agar plates for growth under selection conditions.

Screening for recombinant plasmids was carried out at 5 micrograms/ml tetracycline for transformation into the Hind III site. A selected recombinant, designated pAU-1, was isolated. Crude plasmid preparations of 2 μg-5 μg DNA isolated from pAU-1 were digested with an excess of Hsu I endonuclease. EDTA-$Na_2$ 10 mM, and sucrose 10% w/v (i.e., weight to volume), final concentration were then added and the mixture resolved on an 8% polyacrylamide gel. The DNA was found at a position corresponding to about 410 base-pairs in length.

The relative frequency of transformation by non-recombinant plasmids was measured, comparing alkaline phosphatase pretreated DNA with untreated DNA. Pretreatment reduced the relative frequency of transformation by non-recombinant plasmids to less than 1 in $10^4$ that of non-treated DNA.

EXAMPLE 2

The purification of a nucleotide sequence fragment approximately 550 base-pairs in length comprising a portion of the coding region for human chorionic somatomammotropin (HCS) is described, together with a method of measuring the purity of the isolated sequence. The purified fragment is demonstrated to be greater than 99% pure.

Purification of Human HCS cDNA

Polyadenylated placental RNA isolated as described in copending application Ser. No. 836,218, incorporated herein be reference, was enriched for HCS mRNA by sedimentation in a 5% to 20% (w/v) sucrose gradient at 4° C. in the SW 27 rotor of a Beckman Instruments ultracentrifuge at 25,000 rpm for 16 hours. The 11S-14S region of the gradient was pooled and 100 μg of this RNA used for the synthesis of double-stranded cDNA as described by Ullrich, A., et al., Science 196, 1313 (1977). Synthesis of the second strand was stopped by extraction of the reaction mixture with one volume of ethanol at −70° C. Digestion of the cDNA with HaeIII endonuclease was carried out in 50 μl of 6 mM Tris-HCl, pH 7.5, 6 mM $MgCl_2$, 6 mMβ-mercaptoethanol with 2 units of HaeIII enzyme at 37° C. for two hours, following which 0.1 units of bacterial alkaline phosphatase were added and digestion continued at 60° C. for ten minutes. Following extraction with one volume of phenol-chloroform, the DNA was precipitated with two volumes of ethanol −70° C., dissolved in 20 μl of 10 mM Tris-HCl, pH 8, 1 mM EDTA, and subjected to electrophoresis on a 6% (w/v) polyacrylamide gel. FIG. 1(F) shows the electrophoresis pattern of the foregoing reaction mixture, which reveals a prominent band corresponding to a nucleotide sequence approximately 550 base-pairs in length. The 550 base-pair fragment was excised from the gel, and eluted electrophoretically, with the result shown in FIG. 1(E).

The remaining material corresponding to the 550 base-pair fragment shown in FIG. 1(E) was digested with 4 units of HhaI endonuclease in 50 μl of the same buffer used for digestion with HaeIII endonuclease, at 37° C. for 2 hours. Following phenol-chloroform extraction and ethanol precipitation, the digestion products were separated by electrophoresis on a 6% (w/v) polyacrylamide gel. The result is shown in FIG. 1(D).

The two fragments were eluded electrophoretically, combined and rejoined by incubation in 20 μl of 66 mM Tris-HCl, pH 7.6, 6 mM $MgCl_2$, 15 mM dithiothreitol, 1 mM ATP containing 20 μg/ml of T4 DNA ligase at 15° C. for two hours. The reaction mixture was then diluted to 200 μl with 0.1 M NaCl, extracted with 1 volume of phenol-chloroform and the DNA precipitated with 2 volumes of ethanol. After resuspension in 20 μl of 10 mM Tris-HCl, pH 8, 1 mM EDTA, the ligation products were separated by electrophoresis in the 6% (w/v) polyacrylamide gel. The result is shown in FIG. 1(C). It can be seen from the electrophoresis pattern of FIG. 1(C) that the 550 nucleotide fragment was reconstituted by the ligation treatment. The prior treatment with alkaline phosphatase insured that the two HhaI fragments were rejoined in the original sequence relative to each other to reconstitute the 550 nucleotide segment. The additional bands seen in FIG. 1(C) were the result of dimer formation between the HhaI fragments, since dimer formation is not prevented by the alkaline phosphatase treatment.

The reconstituted 550 nucleotide fragment was excised from the gel and eluted electrophoretically. The electrophoresis pattern of the eluted material is shown in FIG. 1(B). FIG. 1(A) represents the electrophoresis pattern of $^{32}$P-labeled HaeIII digest of double-stranded M13 DNA used as a size marker. The electrophoretic analyses were conducted in a 6% (w/v) polyacrylamide gel in 50 mM Tris-borate, pH 8, 1 mM EDTA at 100 volts for two hours. Following electrophoresis, the gel was dried and exposed to Kodak NS2T x-ray film to produce the autoradiograms.

GENERAL CONCLUDING REMARKS

The above-described method for reducing the frequency of unwanted combinations in a DNA joining reaction will have wide utility in applications of recombinant DNA technology. Two uses have been described herein, the reduction of plasmid ring closure without recombination, and the cleavage of linear DNA followed by reassembly of the sub-fragments in the original sequence. It is anticipated that additional applications of the method of the present invention will be found, within the scope of ordinary skill in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the esssential features hereinbefore set forth, and as follows in the scope of the appended claims.

What is claimed is:

1. A method of transferring a segment of DNA having cohesive ends having 5'-phosphate termini into a microorganism comprising:
    preparing a plasmid DNA having cohesive ends complementary to the cohesive ends of the segment of DNA, and having 5'-phosphate termini,
    subjecting the plasmid DNA to the action of alkaline phosphates in order to provide 5'-hydroxyl termini,
    mixing the plasmid DNA having 5'-hydroxyl termini and the segment of DNA having 5'-phosphate termini in order to form a recombinant DNA,
    mixing the recombinant DNA with a microorganism, in order to transform the microorganism and thereby transferring the segment of DNA to the microorganism.

2. A method for preparing a recombinant plasmid DNA comprising:
    incubating a plasmid DNA with a restriction endonuclease capable of cleaving the plasmid DNA with formation of cohesive ends,
    incubating the cleaved plasmid DNA with an enzyme capable of hydrolyzing phosphate ester groups at the ends of the cleaved plasmid DNA in order to produce 5'-hydroxyl termini,
    mixing the cleaved plasmid DNA having 5'-hydroxyl termini with a heterologous DNA having 5'-phosphate termini and having cohesive ends complementary to the cohesive ends of the plasmid in order to form a heterologous DNA-plasmid DNA complex, and
    subjecting the complex to the action of an enzyme capable of forming a covalent bond between the heterologous DNA and the plasmid DNA, and thereby forming a recombinant plasmid.

3. A method of transferring a segment of cDNA having cohesive ends having 5'-phosphate termini into a microorganism comprising:
    (a) preparing a plasmid DNA having cohesive ends complementary to the cohesive ends of the segment of cDNA and having 5'-phosphate termini,
    (b) subjecting the plasmid DNA to the action of alkaline phosphatase in order to provide 5'-hydroxyl ends on the plasmid DNA, then
    (c) mixing the plasmid DNA having 5'-hydroxyl termini and the segment of cDNA in the presence of an enzyme capable of forming a phosphodiester bond between a DNA strand having a 5'-phosphate end and another DNA strand having a 3'-hydroxyl end in order to form a recombinant DNA,
    (d) mixing the recombinant DNA with a microorganism in order to transform the microorganism and thereby transferring the segment of cDNA to the microorganism.

4. The method of claim 3 wherein step (a) comprises incubating a plasmid DNA having a closed ring structure with a restriction endonuclease capable of cleaving the plasmid ring with concomitant production of cohesive ends complementary to the cohesive ends of the cDNA.

5. The method of claim 3 wherein the microorganism is a bacterium.

6. The method of claim 3 wherein the microorganism is the bacterium *Escherichia coli*.

7. A method for joining DNA molecules having reactant ends capable of being joined in a ligase catalyzed reaction, whereby a selected portion of the reactant ends are prevented from joining to each other comprising:
    pretreating a selected portion of the reactant ends with a reagent capable of removing the 5' terminal phosphate groups therefrom,
    incubating the DNA molecules having pretreated and untreated reactant ends together with a DNA ligase enzyme, whereby a joining reaction is catalyzed between said reactant ends, except that the pretreated reactant ends are not joined to each other by the ligase-catalyzed reaction.

8. A method according to claim 7 wherein the reagent for pretreating the reactant ends is alkaline phosphatase.

9. A method according to claim 8 wherein the DNA molecules to be joined comprise a mixture of restriction endonuclease treated plasmid DNA and non-plasmid linear DNA, and the portion selected for pretreatment comprises the plasmid DNA, whereby end-to-end joining of the plasmid DNA in the absence of recombination with the non-plasmid DNA, is prevented.

10. A method according to claim 8 wherein the DNA molecules to be joined comprise linear sub-fragments of restriction endonuclease treated linear DNA and the reactant ends selected for pretreatment are those occurring on the linear DNA prior to the restriction endonuclease treatment, whereby the joining of the sub-fragments in the wrong sequence is prevented.

* * * * *